United States Patent
Lahtinen et al.

(10) Patent No.: US 6,833,054 B2
(45) Date of Patent: Dec. 21, 2004

(54) METHOD AND APPARATUS FOR ADJUSTING CHEMICAL DOSAGE OF PULP PROCESSING STAGE

(75) Inventors: Juri Lahtinen, Tampere (FI); Jari Kapanen, Lempäälä (FI); Pentti Heino, Lempäälä (FI)

(73) Assignee: Metso Automation Oy, Helsinki (FI)

( * ) Notice: Subject to any disclaimer, the term of this patent is extended or adjusted under 35 U.S.C. 154(b) by 0 days.

(21) Appl. No.: 10/271,258

(22) Filed: Oct. 15, 2002

(65) Prior Publication Data

US 2003/0070778 A1 Apr. 17, 2003

(30) Foreign Application Priority Data

Oct. 16, 2001 (FI) ............................................. 20012009

(51) Int. Cl.⁷ ................................................. D21C 7/14
(52) U.S. Cl. ........................... 162/49; 162/183; 162/62; 162/DIG. 10; 162/236; 700/266; 700/127; 700/128; 700/129
(58) Field of Search ..................... 162/49, 62, DIG. 10, 162/238, 183; 700/266, 127, 128, 129

(56) References Cited

U.S. PATENT DOCUMENTS 6,153,050 A 11/2000 Savoie et al.
6,398,908 B1 * 6/2002 Hermansson et al. ......... 162/65

FOREIGN PATENT DOCUMENTS

| CA | 999950 | 11/1976 |
|---|---|---|
| WO | WO-98/28488 | 7/1998 |

OTHER PUBLICATIONS

Kumpati S. Narendra, Jeyendran Balakrishnan and M. Kemal Ciliz; *Adaptation and Learning Using Multiple Models, Switching and Tuning*; IEEE Control Systems; Jun. 1995; pp. 37–51.

Jukka Perala and Ray Kirby; *Advanced Sequence Kappa Factor Control, Part I: DE Kappa Control*; Tappi Journal; p. 67; vol. 84, No. 4.

Ryozo Nagamune and Shigeru Yamamoto; *Model Set Validation and Update for Time–Varying SISO Systems*; Proceedings of the American Control Conference; Jun. 1998; Pates 2361–2365; Philadelphia, PA.

Copy of Official Action for Finnish Priority Appl. No. 20012009, dated Jun. 11, 2002.

* cited by examiner

Primary Examiner—Peter Chin
Assistant Examiner—Mark Halpern
(74) Attorney, Agent, or Firm—Alston & Bird LLP

(57) ABSTRACT

A method and an apparatus for adjusting a chemical dosage of a pulp processing stage. The method comprises measuring a change in a variable in dependence on the chemical dosage and the chemical dosage to be added, and determining a model describing the change in the variable as a function of the chemical dosage. A performance index is determined for the new model to be compared with the performance index of certain previously determined models. The model that produced the best performance index is put to use.

16 Claims, 2 Drawing Sheets

METHOD AND APPARATUS FOR ADJUSTING CHEMICAL DOSAGE OF PULP PROCESSING STAGE

BACKGROUND OF THE INVENTION

1) Field of the Invention

The invention relates to a method for adjusting a chemical dosage of a pulp processing stage, the method comprising determining the value of a variable in dependence on the chemical dosage prior to adding the chemical dosage, measuring the chemical dosage to be added, determining the value of the variable after adding the chemical dosage, determining, on the basis of the above-mentioned stages, the change in the variable caused by the chemical dosage, determining a model describing the change in the variable as a function of the chemical dosage.

The invention further relates to an apparatus for adjusting a chemical dosage of a pulp processing stage, the apparatus comprising means for determining the value of a variable in dependence on the chemical dosage prior to and after adding the chemical dosage, means for measuring the chemical dosage, calculation means for determining a model describing the change in the variable as a function of the chemical dosage.

The invention relates to adjusting a pulp processing stage, wherein pulp refers to cellulose containing pulp used as a raw material in the manufacture of paper, rayon or the like. The invention particularly relates to adjusting a chemical dosage of a processing stage in a pulp bleaching process.

2) Description of Related Art

As is well known, the purpose of pulp bleaching is to enhance the brightness and cleanliness of pulp by removing colored substances therefrom or by changing such constituents so as to achieve the desired end brightness. Pulp is bleached to a certain level of brightness which depends on the use of the pulp. An important aim of the bleaching process is to keep the brightness level of the bleached pulp as even as possible.

The most significant colored substance of chemically manufactured pulp, i.e. chemical pulp, is residual lignin, which is to be removed from the pulp as completely as possible, in other words pulp is bleached in a manner almost exclusively removing lignin.

The color of pulp can also be bleached in a so-called lignin-saving bleaching process; typically, this method is used in the manufacture of mechanical pulps.

It goes without saying that a bleaching process has to be implemented in an as economical and environmental-friendly manner as possible. The bleaching process is responsible for most of the water consumed and the waste water produced by a sulphate cellulose mill, which makes the role of the bleaching process even more important as regards the environmental load caused by the entire mill. Therefore, the environmental load caused by the chemicals used in bleaching is to be reduced. Such chemicals are also responsible for incurring considerable raw material costs. It is thus extremely important to administer chemical dosages appropriately in order to be able to produce pulp in an environmental-friendly and economical manner.

Conventionally, a chemical dosage of a pulp bleaching process is adjusted by means of a compensated brightness expression feedforward control based on brightness and residual measurements. The method enables suitable dosage adjustment to be achieved in connection with a conventional run, i.e. when chlorine gas is used in the bleaching process. However, the behavior of pulp will eventually undergo changes, and the compensated feedforward does not necessarily respond to these changes. The change in the behavior of the pulp may be short-term, due to e.g. a pulp cooking or washing stage, or it can be more permanent, due to e.g. the characteristics of the raw wood material. A chemical dosage based on the conventional feed-forward is thus not necessarily optimal for a particular situation, which means that the cost-effectiveness and environmental friendliness of the process are reduced and the quality of the pulp becomes uneven.

A method is known from U.S. Pat. No. 6,153,050 for optimizing a chemical dosage of the first stage of a bleaching process. The method is based on a fixed model modeling the reaction cinetics of the chemical used, measuring the characteristics of pulp prior to and after the bleaching stage. On the basis of the model and the measurements, the necessary chemical dosage is determined; if desired, the dosage can be modified by an operator. Since the model is a fixed one, being thus based on the reaction cinetics of a chemical, it does not always describe a real situation in a correct manner because all factors affecting the situation cannot be taken into account by the model.

The method disclosed in CA Patent 999 950 for adjusting a bleaching process applies a model derived from laboratory tests and based on the reaction cinetics of a chemical, the parameters of the model being determined by simulation. This model does not always describe a real situation correctly, either because a real situation under pulp mill conditions also comprises several other factors than those that can be taken into account in the model.

The method disclosed in WO 98/28488 for controlling a bleaching process uses neural networks for modeling the bleaching stage. The modeling examines continuous electromagnetic spectra measured from pulp that are used for providing characteristic quantities for the pulp. On the basis of both the characteristic quantities and laboratory measurements, a process model describing the behavior of the pulp is determined. The method is complex, an essential part of determining the model consisting of time-consuming laboratory measurements that do not necessarily describe the characteristics of the pulp being adjusted under pulp mill conditions.

An article titled "Advanced sequence kappa factor control, Part I: DE kappa control"by Perala and Kirby, TAPPI Journal, Vol. 84, No. 4, p. 67, discloses a method utilizing model predictive control (MPC) in adjusting a chemical dosage of the first two stages in a bleaching plant. The method comprises providing a predictive process model and continuously measuring the kappa number of pulp. This method does not enable correct control, either since the fixed model of the method is incapable of taking all failure situations of the process into account.

An object of the present invention is to provide a novel and improved method and apparatus for adjusting a chemical dosage of a pulp processing stage.

BRIEF SUMMARY OF THE INVENTION

The method of the invention is characterized by determining a performance index for the model, comparing the performance index of the model with the performance indices of certain previously determined models, bringing into use the model that produced the best performance index in the comparison, and determining the necessary chemical dosage by means of the model put to use.

Furthermore, the apparatus of the invention is characterized in that the apparatus further comprises means for determining a performance index for the model, means for comparing the performance index of the model with the performance indices of certain previously determined models, and means for bringing into use the model that produced the best performance index in order to determine the chemical dosage.

The idea underlying the invention is that a performance index is determined for a model, the performance index of the model is compared with the performance indices of certain previously determined models, the model that produced the best performance index in the comparison is brought into use, and the necessary chemical dosage is determined by means of the model put to use. The idea underlying an embodiment of the invention is that the performance of a new model is tested with respect to the models in a model bank by arranging the models in measurement data about the change in a variable caused by a chemical dosage, the measurement information being located in a certain history window, and that the new model is introduced into the model bank if the error produced by the model is smaller than an error produced by a previously determined model taken into account in the comparison, and the model that produced the largest error is removed from the model bank. Furthermore, the idea underlying another embodiment of the invention is that the model is linear in terms of parameters, and that the model is determined using linear regression. Furthermore, the idea underlying still another embodiment of the invention is that the number of model banks is two or more, and that in connection with a current run, a model bank specific to the current run is put to use.

An advantage of the invention is that the adjustment of a chemical dosage becomes more accurate since the model is updated according to the special characteristics of the pulp just being run. When the kind of raw material is changed, the specific model banks enable a model appropriate for a new run to be selected immediately. A further advantage of the invention is that it is simple to implement, and that it can be applied to different pulp processing stages in a versatile manner. A further advantage is that only the decisive aspect, i.e. the bleaching of pulp, is measured.

BRIEF DESCRIPTION OF THE SEVERAL VIEWS OF THE DRAWINGS

The invention will be explained in closer detail in the accompanying drawings, in which.

DETAILED DESCRIPTION OF THE INVENTION

Figure 1:
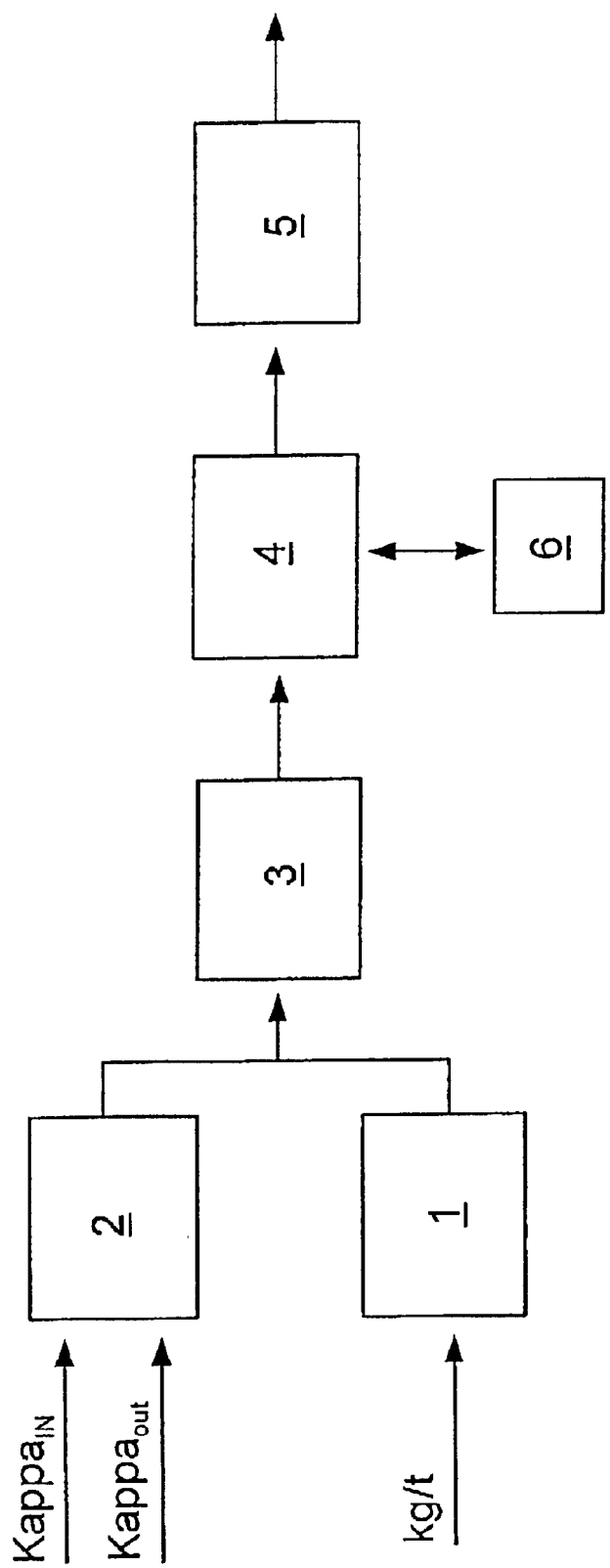
FIG. 1 is a schematic view showing method steps of an embodiment of a method in accordance with the invention.

FIG. 1 is a schematic view showing the method steps of an embodiment of a method in accordance with the invention. In a first method step 1, chemical dosages added to pulp, e.g. kilogram per pulp ton (kg/t), are stored into memory from a processing stage.

A second method step 2 comprises calculating a change in a variable in dependence on a chemical dosage of the processing stage. The variable is now the kappa number of the pulp by way of example but, of course, the variable may also be something else.

A kappa number is the measure of the amount of lignin remaining in the pulp. As the kappa number decreases, the bleachability of pulp increases. Now, the change in the variable is thus the difference of input kappa $Kappa_{IN}$ and output kappa $Kappa_{OUT}$, i.e. kappa reduction. An input kappa is a kappa number measured from the pulp supplied to a particular processing stage, i.e. the kappa number prior to adding a chemical dosage to the pulp in the processing stage. An output kappa is the kappa number measured from the pulp removed from the particular processing stage, i.e. the kappa number after adding the chemical dosage in the particular stage. The second method step thus provides information on the bleachability of the pulp, indicated as a kappa reduction.

A third method step 3 comprises providing a model between the bleachability of the pulp and the chemical dosage. The model is calculated in a particular history window, which can be determined e.g. on the basis of the measurement time to be taken into account therein. In connection with the application examples of the present application, a history window refers to an 8-hour-long time span comprising information measured during this time on the chemical dosages added to the pulp as well as on the bleaching of the pulp. A history window is a sliding window, meaning that the window slides along with time.

The model is calculated using linear regression, the result being a linear model for bleachability as a function of a chemical dosage. The result is a linear model at least in terms of parameters. The parameters of a new model, i.e. an angular coefficient and a constant factor, are stored in memory in a model bank.

A fourth method step 4 comprises examining the performance of the new model. Preferably, the time delay between calculating the new model in the method step 3 and examining the performance of the model is as long as the history window. In other words, the performance examination of the new model is started only when the history window no longer contains the same information as that used for calculating the model in the third method step 3. The delay is now eight hours.

The bleaching of the pulp is modeled continuously. Each time new information on the process is obtained, i.e. each time the kappa reduction or the bleaching of the pulp is calculated, in principle a slightly different model than that based on the previous history information is obtained. If the kappa reduction or the bleaching of the pulp is calculated e.g. every half an hour, the history window in the present application example being eight hours, the new model can be calculated using linear regression directed at a 16-member point family.

The performance of the new model is examined in a performance comparison taking place on the basis of relevant history information. In the performance comparison, the new model is compared with the models stored in a model bank 6 that, according to previous experience, have described the behavior of the pulp in the most appropriate manner. The model bank thus comprises models that are at least moderately well suited for a current run. The number of models in a model bank can be selected appropriately. In the present embodiment, ten best models have been stored in the model bank.

In the performance examination, a performance index is determined for a model in an appropriate manner. The performance index is determined based e.g. on calculating the least squarest of an error across an entire history window. If it turns out that the new model produces a smaller error, i.e. the performance index of the new model is better than that of a model stored in the model bank, the new model is introduced into the model bank. Similarly, the model in the model bank that produces the largest error, i.e. the worst performance index, is removed from the model bank. The number of models in the model bank thus remains constant. The control of the process being run starts using the model that produces the smallest error: either the newest one or any one of the nine old ones. If the performance examination indicates that the new model produces a larger error than those produced by the models in the model bank, the new model is removed, and the model that produces the smallest error, which is a model among the models in the model bank, is put to use. The performance index may also be based e.g. on a mean error, error variance, correlation, time or the like.

A fifth method step 5 comprises calculating, on the basis of the model selected for use, the chemical dosage for feedforward. The calculation takes into account a target value which has been set for the process being controlled and according to which the pulp leaving the process is to be. The target value may be expressed e.g. as the brightness of the pulp or as a kappa reduction. Preferably, the input kappa or the brightness of the pulp supplied to the process is measured continuously. On the basis of the input kappa or the brightness of the pulp supplied to the process and the post-process target value, the necessary change in bleaching and, on the basis of a model further calculated therefrom, the magnitude of a chemical dosage to be fed into the pulp at a given time are determined.

As was already stated above, the bleaching of the pulp is modeled continuously. The model used is updated in real time, and it quickly adjusts itself to a current run. Thus, the method is not based on prediction but the parameters of the model used are selected on the basis of history information. When determining the magnitude of an optimal chemical dosage, no need exists to find out the ultimate reasons for the behavior of the pulp and make assumptions related thereto. The only assumption is now that particularly within a short period of observation and within a normal working range, the behavior of the pulp can be described by a model which is linear at least in terms of parameters.

Figure 2:
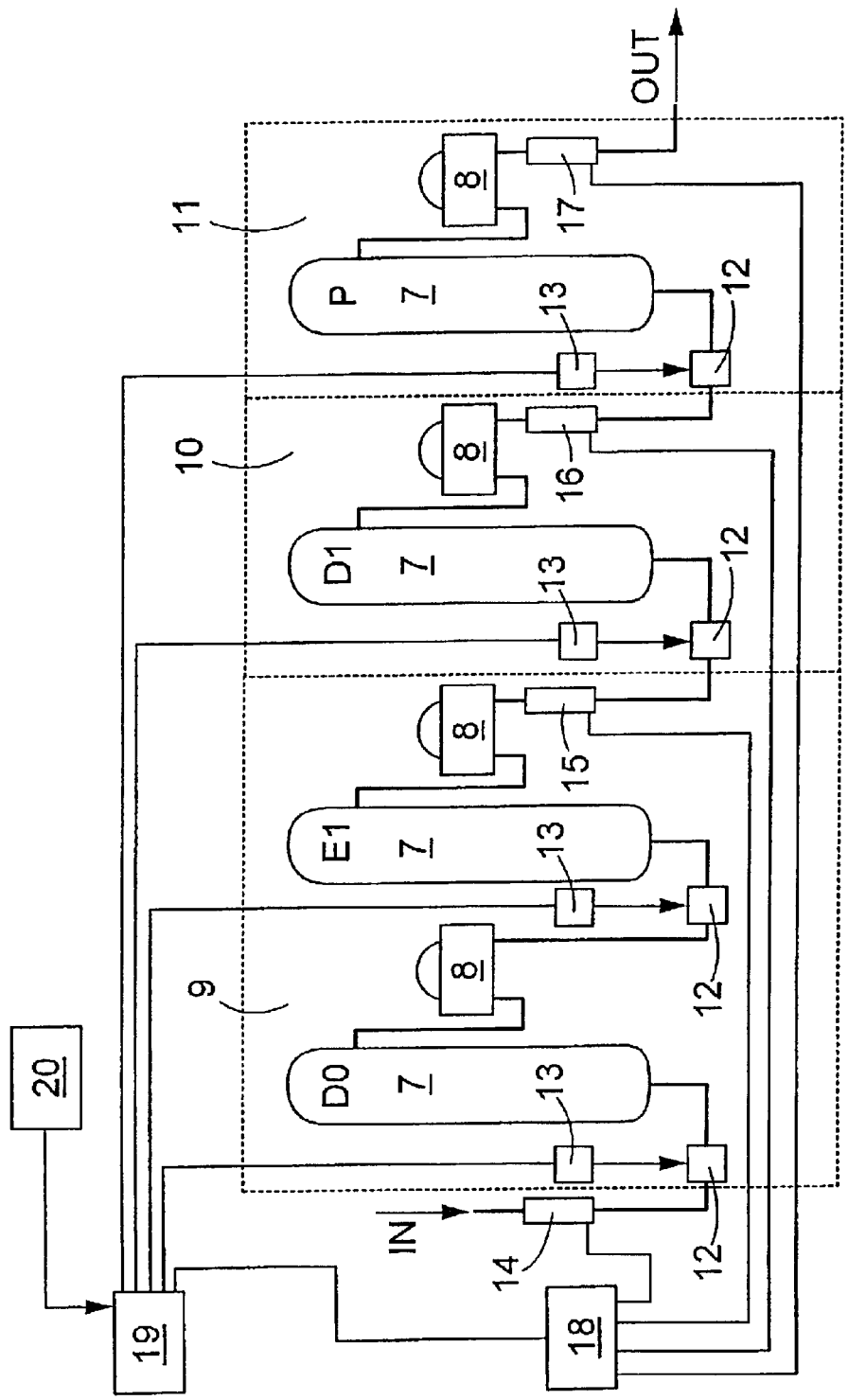
FIG. 2 is a schematic view showing another embodiment of the method and apparatus in accordance with the invention as arranged in a pulp bleaching plant.

FIG. 2 is a schematic view showing another embodiment of the method and apparatus in accordance with the invention as arranged in a pulp bleaching plant. It is to be noted that the invention is applicable both to ECF (Elementary Chlorine Free) and TCF (Totally Chlorine Free) pulps. In addition to sulphate pulps, the invention can be applied in connection with sulphite pulps.

According to their structure, the apparatuses in bleaching plants can be divided into three groups:
1. tower bleaching plants: each bleaching stage takes place in a separate reaction tower 7, the washing between the stages being conducted by separate washers 8 outside the towers,
2. diffuser bleaching plants: each bleaching stage takes place in a separate reaction tower, the washing between the stages being conducted by diffuser washers arranged at top end of the towers, and
3. displacement bleaching plants: several bleaching stages take place in a single tower, pulp being washed between the stages by diffuser washing units built inside the tower.

The reaction tower 7 may be pressurized or atmospheric. Being well known per se to one skilled in the art, the operation and structure of bleaching apparatuses will not be discussed in greater detail in the present application.

The operation of a tower bleaching plant shown in FIG. 2 is divided into three processing stages 9, 10 and 11, each stage comprising adding at least one chemical to the pulp. The chemical is added by chemical feeders 12 known per se that are controlled by dosage adjusters 13 known per se. A processing stage typically comprises one or two bleaching sequences. A processing stage mainly operates in the following manner:

1. adjusting pulp consistency
2. adding chemical dosage to pulp flow
3. adjusting reaction temperature and pH,
4. reactions of chemicals and pulp
5. washing or eluating reaction products and residual chemicals from pulp flow before next processing stage.

The chemical feeders 12 continuously add chemicals to the pulp. The pulp delay time between adding a chemical dosage and measuring the output kappa or the brightness is known, which means that the magnitude of the bleaching of the pulp caused by the short-term chemical dosage is thus also known.

The first processing stage 9 of the bleaching plant of FIG. 2 comprises a first chlorine dioxide sequence D0 and a first sodium hydroxide stage E1. In a specified manner, the magnitude of a sodium hydroxide dosage is proportional to the amount of a chlorine dioxide dosage, in other words determining the chemical dosage of the first sequence D0 indirectly means determining the chemical dosage of the second stage E1 as well. The second processing stage 10 comprises a second chlorine dioxide sequence D1 and the third processing stage 11 comprises a hydrogen peroxide sequence P.

The bleaching of the pulp taking place in the processing stage can be determined not only by the above-described kappa number reduction but also as a difference of input and output brightnesses, i.e. as a change in brightness, or by another known method known per se.

In the bleaching plant, the brightness of the pulp can be measured at four different points: the first stage input kappa at a first point 14 and the output kappa at a second point 15; the second stage input brightness at the second point 15 and the output brightness at a third point 16; the third stage input brightness at the third point 16 and the output brightness at a fourth point 17. An increase in the brightness of the pulp caused by each processing stage constitutes the difference of the output and input kappas or the difference of the input and output brightnesses of a particular stage.

The output kappa or the output brightness of the processing stage 9 to 11 is the measurement result of a variable after adding a chemical dosage in the particular stage, i.e. the measurement result of the variable measured from the pulp being removed from the particular processing stage. In the first stage of the bleaching process, bleaching usually takes place by removing lignin; this is measured by a kappa number reduction. Towards the end of the bleaching process, the amount of lignin is typically highly reduced; therefore, the bleaching is generally based on the bleaching of the pulp constituents, the brightness of the pulp being determined as its reflectivity as measured by a certain wave length.

The kappa numbers and the brightnesses are measured by an analyzer 18. Naturally, the necessary measurements can also be carried out by other measuring devices known per se, such as electrochemical devices, or as laboratory analyses.

The operation of the analyzers 18 and other measuring devices will not be described in closer detail herein.

The chemical dosages of the bleaching plant are adjusted according to the method described in connection with FIG. 1. In the embodiment shown in FIG. 2, a control unit 19 comprises means for calculating a new model on the basis of the information about a change in the value of a variable supplied from the analyzer 18 and the information about the chemical dosages supplied from the dosage adjusters 13. The control unit 19 further comprises means for calculating the model that produces the smallest error and bringing it into use, and for removing the worst model from the model bank. The control and supervision of bleaching plants are highly automated, more often than not being implemented by a distributed control system. The means of the apparatus of the invention may be arranged in the control system in various ways. The method of the invention can be implemented by software by a computer software code to be run on a processor and stored in an internal memory means of the apparatus or arranged to be retrieved to the apparatus from an external memory means, such as a CD-ROM or an information network. The method can also be implemented as a hardware solution or as a combination of such a solution and a software solution.

The control unit 19 also comprises the necessary model banks. Preferably, the number of model banks associated with the bleaching plant is more than one; for instance, each particular kind of wood is provided with a model bank of its own. This is because the bleaching characteristics of different kinds of wood differ from each other to such an extent that the models determined for one kind of wood do not give an optimal result if used for pulp made of another kind of wood. A model bank is thus specific with regard to the kind of wood. When the kind of raw material, i.e. the kind of wood, changes, the model that produces the smallest error is put to use from the model bank of the particular kind of wood. In order to determine such a model, a history window originating from the previous run of the particular wood is used. Preferably, selecting a model bank, selecting a model from the model bank on the basis of a performance examination, and putting the model to use are all carried out as automatized operations which, in a normal situation, can be ignored by an operator. It is, however, preferable to disclose e.g. the magnitude of a chemical dosage at a user interface of the operator because this makes it possible for the operator to follow the operation of a process and, if necessary, interfere with the process.

A model bank may also be specific with regard to another factor affecting a current run. It may be e.g. quality-specific, i.e. depend on the end product to be manufactured, specific with regard to the target aim for the brightness of pulp, temperature-specific, season-specific, depend on the dirtiness of the process equipment or the history of the pulp, i.e. depend on a measurable or otherwise determinable factor.

The magnitude of a chemical dosage is adjusted using an adaptive model, i.e. a model which adapts itself to an acute process situation. Naturally, a process situation is affected by numerous factors, but they are included in the model; it is thus unnecessary to know or model such factors separately. The point is simply to measure the magnitude of a chemical dosage of a particular processing stage and a change in the value of a variable in dependence on the chemical dosage. Of course, variables that are known to be measured from the process can be and preferably are measured for the needs of the rest of control and supervision of the process.

In the embodiment shown in FIG. 2, the bleaching plant is further controlled by feedback based on fuzzy logic. A feedback system 20 comprises measuring the brightness and pH of the pulp and the amount of residual chemicals in the pulp. The feedback takes into account the delay time of the processing stage, brightness target value and the effect of running speed on the target. If necessary, the feedback adjusts the chemical dosage determined by the feedforward. The feedback can optionally be used to complement the feedforward adjustment of the invention.

The drawings and the related description are only intended to illustrate the idea of the invention. In its details, the invention may vary within the scope of the claims. The invention can thus also be applied to other pulp bleaching processes, i.e. processes wherein the brightness of the pulp is increased either directly or indirectly. Such processes include e.g. an oxygen delignification stage of pulp, bleaching of mechanical pulps and enzyme bleaching. In oxygen delignification, lignin is oxidized and broken down to make it soluble with alkali (oxidized with white liquor). The groups producing dark color, i.e. absorbing light, also called chromophores, in unbleached pulp mainly reside in lignin. In the bleaching process of mechanical pulps, either oxidizing hydrogen peroxide or sodium peroxide or reducing dithonite is added to the pulp. The aim in bleaching is to make the colored groups of substances, i.e. chromophores, in the pulp uncolored. In enzyme bleaching, the enzyme added to the pulp reacts e.g. with hemicellulose or residual lignin. Depending on the enzyme, the pulp either becomes brighter or its characteristics change such that other chemicals react better with lignin. The chemical to be adjusted may be other than any of those disclosed above, such as $Cl_2$, $NaOCl$, $O_2$, $O_3$, $Na_2O_2$. The invention can also be applied to the pH adjustment of pulp processing stages, wherein the chemical may be e.g. sulphur dioxide $SO_2$, sulphuric acid $H_2S_4$, sodium hydroxide $NaOH$ or the like.

That which is claimed:

1. A method for adjusting a chemical dosage of a pulp processing stage, the method comprising determining, prior to adding the chemical dosage, a value of a selected variable representing a property of the pulp where the value is dependent on the chemical dosage to be added to the pulp, measuring the chemical dosage to be added, adding the chemical dosage to the pulp, determining the value of the variable associated with the pulp after adding the chemical dosage, determining, on the basis of the above-mentioned steps, the change in the value of the variable caused by the addition of the chemical dosage to the pulp, determining a model describing the change in the variable as a function of the chemical dosage, determining a performance index for the model, where the performance index represents the difference between an output of the model and actual data associated with the process, comparing the performance index of the model with performance indices associated with previously determined models, bringing into use the model that produced the best performance index in the comparison, and determining the necessary chemical dosage by means of the model put to use.

2. The method of claim 1, further comprising determining the performance index of the model in a performance comparison wherein the certain previously determined models constitute a model bank, arranging the models in measurement results of the change in the variable caused by the chemical dosage, the measurement results being located in a certain history window, introducing the new model into the model bank if the performance index of the new model is better than the performance index of any one of the previously determined models taken into account in the comparison, and removing the model that produced the worst performance index from the model bank.

3. The method of claim 1, wherein the value of the variable in dependence on the chemical dosage is determined in real time and the chemical dosage to be added is also measured in real time.

4. The method of claim 1, wherein the model describing the change in the variable as a function of the chemical dosage is determined based on a sliding history window which represents data collected within a certain time period window, where older data from earlier in the time period is removed from the window as new occurring data is added to the window over time.

5. The method of claim 4, wherein the new model is included in the performance comparison only after the measurement information used in determining the particular model has been completely removed from the window by addition of new occurring data to the history window.

6. The method of claim 1, wherein the model is linear at least in terms of parameters, and that it is determined using linear regression.

7. The method of claim 1, wherein the certain previously determined models constitute a model bank, and wherein the model banks are specific with respect to a factor affecting a current run.

8. The method of claim 7, wherein each specific model bank is provided with a history window of its own which is put to use in connection with the particular model bank.

9. The method of claim 1, wherein the pulp is chemical pulp.

10. The method of claims 1 to 8, wherein the pulp is mechanical pulp.

11. The method of claim 1, wherein the process to be adjusted is a pulp bleaching process or any one of the stages thereof.

12. The method of claim 11, wherein the variable is the kappa number of the pulp.

13. The method of claim 11, wherein the variable is the brightness of the pulp.

14. The method of claim 1, wherein the variable is the pH of the pulp.

15. The method of claim 1, wherein the chemical dosage to be adjusted comprises at least one of the following chemicals: $ClO_2$, $Cl_2$, $NaOCl$, $O_2$, $O_3$, $H_2O_2$, $Na_2O_2$, $NaOH$, $SO_2$, $H_2SO_4$, peracetic acid, Caro's acid, enzymes.

16. The method of claim 1, wherein the model describing the change in the variable as a function of the chemical dosage is determined at least every half an hour.

* * * * *